United States Patent
Brunnett

(10) Patent No.: US 7,443,947 B2
(45) Date of Patent: Oct. 28, 2008

(54) METHOD AND APPARATUS FOR IMPROVED RADIATION DETECTION

(75) Inventor: Carl J. Brunnett, Willoughby Hills, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 113 days.

(21) Appl. No.: 10/556,918

(22) PCT Filed: Apr. 19, 2004

(86) PCT No.: PCT/IB2004/001505

§ 371 (c)(1),
(2), (4) Date: Nov. 14, 2005

(87) PCT Pub. No.: WO2004/100792

PCT Pub. Date: Nov. 25, 2004

(65) Prior Publication Data

US 2007/0005278 A1 Jan. 4, 2007

Related U.S. Application Data

(60) Provisional application No. 60/470,316, filed on May 14, 2003.

(51) Int. Cl.
*A61B 6/00* (2006.01)
*G21N 23/00* (2006.01)

(52) U.S. Cl. .............................. 378/19; 378/210

(58) Field of Classification Search ............... 378/4–20, 378/98.2–98.12, 210, 901; 250/395
See application file for complete search history.

(56) References Cited

U.S. PATENT DOCUMENTS

| | | | | | |
|---|---|---|---|---|---|
| 4,008,400 | A | * | 2/1977 | Brunnett et al. | 378/4 |
| 4,048,503 | A | * | 9/1977 | Taylor | 378/19 |
| 4,052,620 | A | * | 10/1977 | Brunnett | 378/97 |
| 4,129,783 | A | * | 12/1978 | Houston | 378/9 |
| 4,157,472 | A | * | 6/1979 | Beck et al. | 378/4 |
| 4,812,848 | A | | 3/1989 | Fry | |
| 5,022,060 | A | * | 6/1991 | Trotel | 378/19 |
| 5,155,752 | A | * | 10/1992 | Kawakami | 378/97 |
| 5,172,115 | A | | 12/1992 | Kerth et al. | |
| 5,229,772 | A | | 7/1993 | Hanlon | |
| 5,457,458 | A | | 10/1995 | Saxon | |
| 5,579,247 | A | | 11/1996 | Kerth et al. | |
| 5,822,369 | A | | 10/1998 | Araki | |
| 5,953,439 | A | * | 9/1999 | Ishihara et al. | 382/107 |
| 6,094,473 | A | * | 7/2000 | Yu | 378/108 |
| 2002/0141530 | A1 | | 10/2002 | Vrettos | |
| 2004/0206909 | A1 | * | 10/2004 | Izumi et al. | 250/395 |

\* cited by examiner

*Primary Examiner*—Edward J Glick
*Assistant Examiner*—Anastasia Midkiff

(57) ABSTRACT

In a method for measuring detected radiation, an analog data signal is converted to a digital data signal having aperiodic data pulses varying with intensity of the analog data signal. A time signal indicative of data intervals is produced. The data pulses are counted. A data count is stored in a start location and a corresponding time value is stored in a start location each time a data pulse occurs until a measured data interval starts. After a next data interval is detected, the data count is stored in an end location and a corresponding time value is stored in an end location when the next data pulse occurs. An average intensity of the detected radiation for the measured data interval is determined from the stored data counts and time values. A CT scanner (10) for measuring detected radiation includes a channel circuit (56), a storage circuit (60), a control circuit (58), and a processor (62).

20 Claims, 5 Drawing Sheets

METHOD AND APPARATUS FOR IMPROVED RADIATION DETECTION

CROSS REFERENCE TO RELATED APPLICATIONS

This application claims the benefit of U.S. provisional application Ser. No. 60/470,316 filed May 14, 2003, which is incorporated herein by reference.

The invention relates to the diagnostic imaging arts. It finds particular application in conjunction with defining measurement periods for data intervals in CT scanners and will be described with particular reference thereto. However, it is to be appreciated that the invention is also amenable to other applications.

Analog/digital (A/D) conversion in a CT scanner utilizes an integrating current to frequency converter (IFC). The IFC is a current-controlled oscillator. The current produced by a detector associated with the CT scanner varies the frequency of the current-controlled oscillator. During a data interval (which is defined by the angular position of a rotating gantry or, more precisely, an arc segment), the IFC pulses are counted, and the time from the first pulse to the last pulse is measured with high precision. The actual measurement is calculated by taking the ratio of the COUNTS to the TIME. The precision of the measurement is high since it is determined by the precision of the TIME count which is produced by counting the pulses from a high frequency oscillator.

In a "delta data" mode of operation, the counting of COUNTS and TIME pulses starts with the last IFC pulse of the preceding data interval and ends with the last IFC pulse of the measured data interval. By allowing the measurement period to extend into the preceding data interval, all the current from the radiation detector is utilized, thus insuring high quantum signal to noise ratio. The "delta data" technique does, however, advance (or skew) the measurement period from its physical arc segment (i.e., data interval). With a large number of COUNT pulses in the data interval, this shift is minimal. If 100 COUNT pulses are counted, the skewing is nominally 0.5%. However, for low signal levels, this skew can be significant. If only one pulse is generated per data interval, the skewing is nominally 50% but can be up to 100%. This data skewing may cause objectionable image artifacts.

A standard ratiometric type A/D conversion (without delta data) requires that at least two COUNT pulses be produced per data interval. When employing delta data this requirement is reduced to one COUNT pulse per data interval. In order to insure that the minimum pulse rate is maintained, an offset dc current is injected into the front end. The counts resulting from this offset current are subsequently subtracted out before taking the ratio of COUNT to TIME. However, the shot noise associated with this offset current increases the input noise of the A/D conversion thus reducing the overall dynamic range of the system.

There is, therefore, a need to improve the accuracy of previous delta data modes by reducing (or eliminating), on the average, the skewing of the measurement period with respect to the measured data interval. There is also a desire to further reduce the required offset current in order to minimize noise and improve the dynamic range of the system.

In one embodiment of the invention, a CT scanner includes a means for rotating a radiation source around an examination region, a means for generating an analog data signal that varies with an intensity of radiation traversing the examination region, a means for converting the analog data signal to a digital data signal including aperiodic pulses varying in frequency with the intensity of the radiation traversing the examination region as the radiation source rotates about the examination region, a means for producing a time signal indicative of data intervals, and a means for determining average radiation intensity in each data interval by counting the pulses of the digital data signal starting with a digital data signal pulse occurring in a preceding data interval and continuing to a digital data signal pulse occurring in a succeeding data interval.

In another embodiment, the invention provides a method of measuring an intensity of detected radiation in a CT scanner. A radiation source is rotated around an examination region. An analog data signal that varies with an intensity of radiation traversing the examination region is generated. The analog data signal is converted to a digital data signal including aperiodic pulses varying in frequency with the intensity of the radiation traversing the examination region as the radiation source rotates about the examination region. A time signal indicative of data intervals is produced. Average radiation intensity in each data interval is determined by counting the pulses of the digital data signal starting with a digital data signal pulse occurring in a preceding data interval and continuing to a digital data signal pulse occurring in a succeeding data interval.

In still another embodiment of the invention, an apparatus for measuring an intensity of a detected radiation in a CT scanner includes a channel circuit which generates time-based digital information from an analog data signal for a measured data interval, the time-based digital information including at least one component of the analog data signal from a preceding data interval and a succeeding data interval, a storage circuit which stores the time-based digital information, a control circuit which determines when to store the time-based digital information, and a processor which determines an average intensity of the detected radiation for the measured data interval from the stored time-based digital information.

One advantage of the invention is the measurement period for a measured data interval is, on the average, centered on the data interval, thus producing an average measurement skew of zero.

Still another advantage is, under conditions of high attenuation, the measurement period is significantly longer than the data interval thus producing more integrated signal, reducing quantum noise, and increasing the system dynamic range.

Yet another advantage is the increase in measurement period as the input signal decreases produces an adaptive filtering effect in the analog domain that can potentially improve image quality by reducing noise more effectively than by subsequently filtering in the digital domain.

Still yet another advantage is, in various embodiments, offset current can be reduced to a point where less than one pulse occurs per data interval. This reduces shot noise associated with the offset current and decreases the effects of quantization noise and 1/f noise. The resulting overall noise reduction improves image quality and extends the dynamic range of the system.

Other advantages will become apparent to those of ordinary skill in the art upon reading and understanding the following detailed description.

The drawings are for purposes of illustrating exemplary embodiments of the invention and are not to be construed as limiting the invention to such embodiments. It is understood that the invention may take form in various components and arrangement of components and in various steps and arrangement of steps beyond those provided in the drawings and associated description. Within the drawings, like reference numerals denote like elements.

Figure 1:
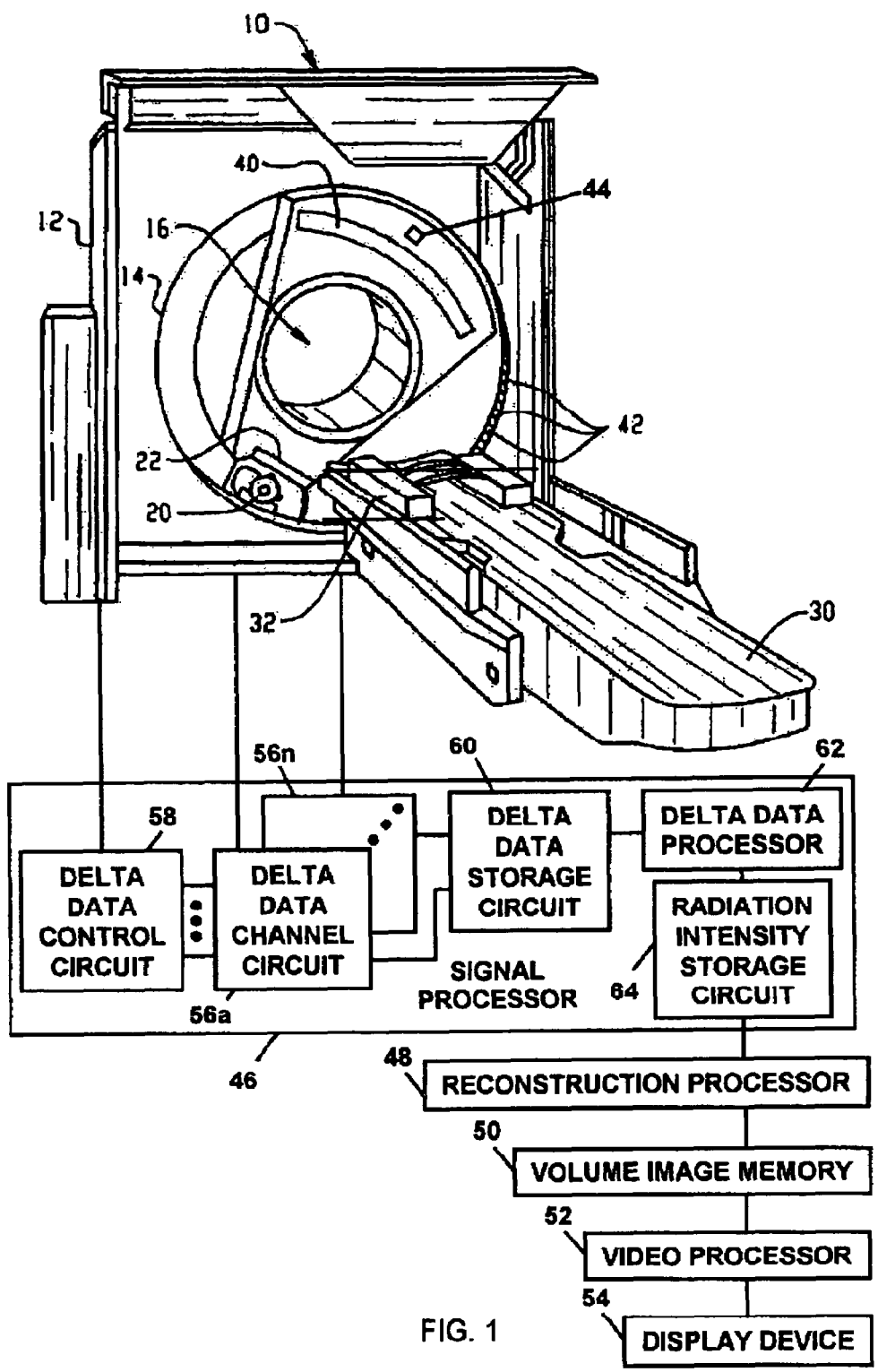
FIG. 1 is a block diagram of an embodiment of a CT scanner incorporating the invention.

With reference to FIG. 1, a CT scanner 10 includes a stationary gantry 12 a rotating gantry 14, an imaging region 16, a radiation source 20, a collimator and shutter assembly 22, a subject support 30, a head restraint 32, a plurality of radiation detectors 40 or 42, an encoder 44, a signal processor 46, a reconstruction processor 48, a volume image memory 50, a video processor 52, and a display device 54.

The stationary gantry 12 and rotating gantry 14 define the imaging region 16. The rotating gantry 14 is supported by the stationary gantry 12 for rotation about the examination region 16. The radiation source 20 (e.g., x-ray tube) is arranged on the rotating gantry 14 for rotation therewith. The radiation source 20 produces a beam of penetrating radiation that spans and passes through the examination region 16 as the rotating gantry 14 is rotated by an external motor (not illustrated) about a longitudinal axis of the examination region 16. The collimator and shutter assembly 22 forms the beam of penetrating radiation into a fan, cone, or wedge shape and selectively gates the beam on and off. Alternately, the radiation beam is gated on and off electronically at the radiation source 20. The patient support 30, such as a radiolucent couch or the like, suspends or otherwise holds a subject being examined or imaged at least partially within the examination region 16 such that the beam of radiation defines a volume through the region of interest of the subject. The head restraint 32 restricts the mobility of the subject's head.

In a third generation CT scanner, an arc or a 2-dimensional array of radiation detectors 40 is mounted peripherally across from the radiation source 20 on the rotating gantry 14. In a fourth generation CT scanner, one or more stationary rings of radiation detectors 42 are mounted around the stationary gantry 12. Regardless of the configuration, the radiation detectors 40, 42 are arranged to receive the radiation emitted from the radiation source 20 after it has traversed the imaging region 16.

The radiation detectors 40, 42 convert the detected radiation into analog data signals. That is, each radiation detector 40, 42 produces an analog data signal that is proportional to an intensity of received radiation.

The signal processor 46 receives the analog data signals from the radiation detectors 40, 42. The signal processor 46 optionally performs filtering and other operations (e.g., generation of time-based digital information and calculation of average radiation intensity per data interval) before passing the data to a reconstruction processor 48 that reconstructs volume image representations of the subject for storage in a volume image memory 50. A video processor 52 under operator control retrieves and formats selected portions of the data for display on a display device 54, printing on a printer, etc. as a slice image, 3-dimensional rendering, or the like.

During each orbit of the rotating gantry 14, the encoder 44 produces an index signal that is transmitted to the signal processor 46 to associate the position or angular arc segments of the rotating gantry with the analog data signals from the radiation detectors 40, 42. Each rotation of the radiation source is broken up into a succession of individual scan segments (i.e., data intervals) as the rotating gantry 14 turns or orbits the subject. In the preferred embodiment the index signal is a series of pulses, with a predetermined amount of pulses for each data interval. The last pulse for each data interval indicating termination of one data interval and initiation of a next or succeeding data interval. In alternate embodiments, devices capable of producing a similar index signal may be used in place of the encoder 44.

The encoder 44 produces an index signal pulse at regular angular intervals, e.g. 0.1 degree. The index signal provides a timing signal defining the beginning and end of successive data intervals.

The signal processor 46 includes a plurality of delta data channel circuits 56*a*-56*n* that are each responsive to individual analog data signals from the radiation detectors 40, 42, a delta data control circuit 58 that is responsive to an index signal from the encoder 44, a delta data storage circuit 60 for accumulating time-based digital information corresponding to the analog data signals, a delta data processor 62, and a radiation intensity storage circuit 64. The delta data channel circuits 56*a*-56*n* are typically identically constructed.

Figure 2:
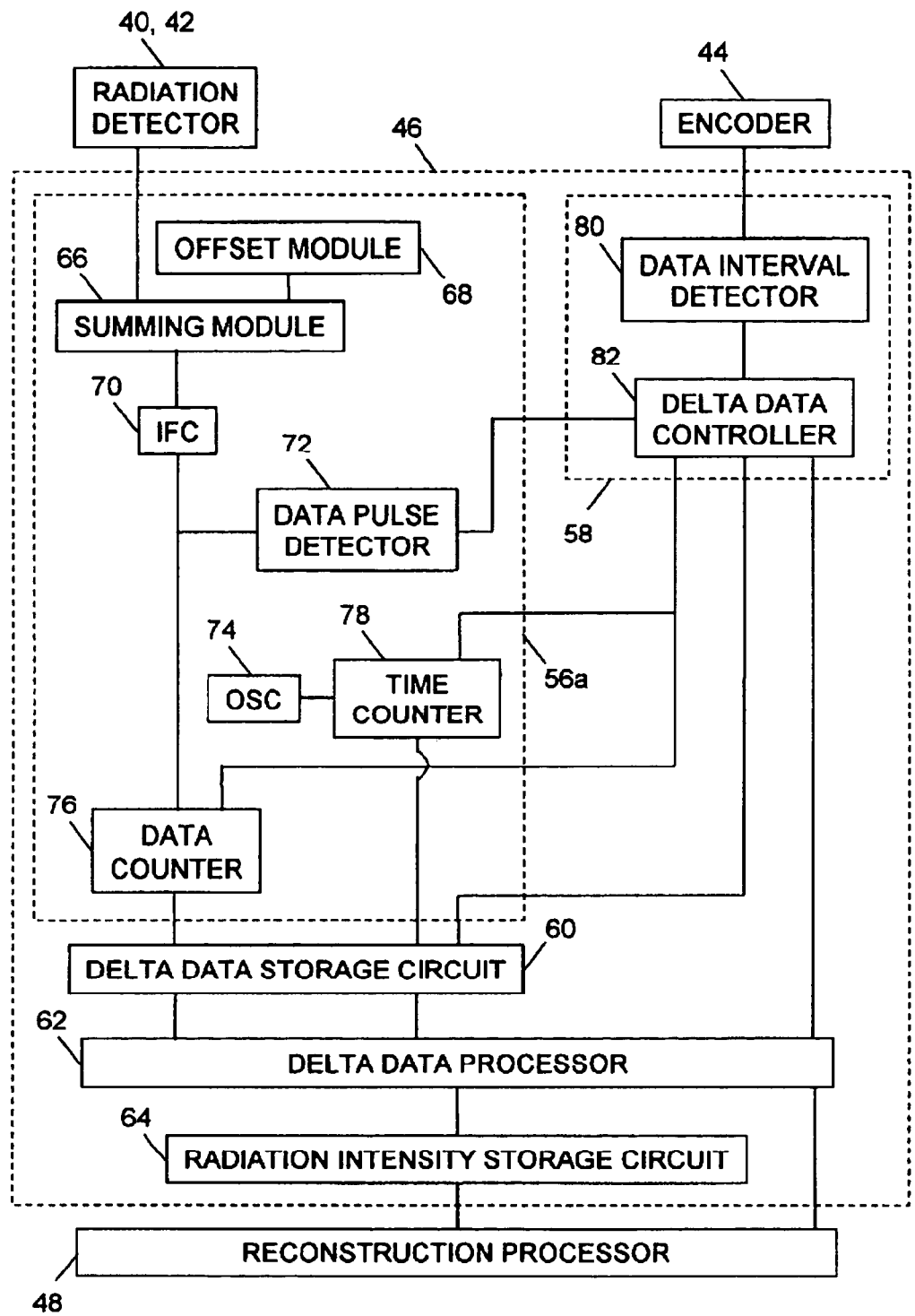
FIG. 2 is a block diagram of an embodiment of a signal processor associated with the CT scanner of FIG. 1.

With reference to FIG. 2, only one delta data channel circuit 56*a* is shown in the signal processor 46 to simplify the description. The delta data control circuit 58 develops time-based digital information in the delta data channel circuit 56*a* corresponding to the analog data signal. This type of conversion may also be referred to as a analog-to-digital (A/D) conversion. In principle, this type of conversion is preferably accomplished using current to frequency conversion (IFC) or voltage to frequency conversion (VFC) techniques. At appropriate times, the delta data control circuit 58 transfers the time-based digital data information from the delta data channel circuit 56*a* to the delta data storage circuit 60 and notifies the delta data processor 62 when the data is ready to be read from the delta data storage circuit 60.

The delta data channel circuit 56*a* includes a summing module 66, an offset module 68, an IFC 70, a data pulse detector 72, a free-running oscillator 74, a data counter 76, and a time counter 78. The delta data control circuit 58 includes a data interval detector 80 and a delta data controller 82.

In summary, the delta data channel circuit 56*a* provides an A/D conversion of the analog data signals by integrating a current output and producing a pulse train of a corresponding frequency. The delta data control circuit 58 monitors the data interval index signal and the output of the IFC 70. During scanning operations, the intensity of the analog data signal inherently varies with tissue density.

In one embodiment, the delta data control circuit 58 stores "start data count" and "start time" for each data interval in response to the last "pulse" of the pulse data signal in the preceding data interval. In this embodiment, the delta data control circuit 58 also stores the "end data count" and "end time" for each data interval in response to the first pulse of the succeeding data interval. The delta data processor 62 determines the number of pulses (i.e., COUNTS) from the difference between the "end data count" and the "start data count" and the difference between "end time" and "start time" (i.e., TIME) for each data interval. The delta data processor 62 divides the COUNTS by the TIME to generate a numeric radiation intensity value for one data interval for one detector. Thus, the measurement period reflected by the COUNTS and TIME for each data interval extends into both the preceding and succeeding data intervals. This is referred to as a symmetrical delta data mode of operation. Although the measurement period extends outside of the measured data interval, on the average, the measurement periods are centered on the measured data intervals. In this manner, the sampling window dynamically widens beyond one data interval with high attenuation. The longer measurement periods reduce noise and increase the S/N ratio during high attenuation (when a higher S/N is most important), thus increasing the overall dynamic range of the A/D conversion. This technique produces a symmetrical variable filtering method for measuring radiation intensity during scanning operations.

In the embodiment being described, the delta data channel circuit 56a preferably guarantees that at least one "pulse" is output from the IFC 70 during each data interval. To accomplish this, the offset module 68 provides an offset current to the summing module 66. The summing module 66 combines the offset current with the analog data signal to produce an offset data signal. Preferably, the current provided by the offset module 68 is adjusted to a minimum level required to guarantee that the IFC 70 generates at least one pulse during each data interval. The data pulse detector 72 monitors the output of the IFC to detect pulses. Each time a pulse is detected, the detected event is communicated to the delta data controller 82.

The IFC 70 provides a digital pulse train output (i.e., pulse data signal) that varies in frequency based on the level of the offset data signal. As such, the pulse data signal is a digital representation of the analog data signal. The pulse data signal is provided to the data counter 76. The data counter 76 counts each pulse and accumulates a "data count." In an alternate embodiment, the "data count" can be based on voltage rather than current. In this alternate embodiment, the IFC is replaced with a VFC.

In the embodiment being described, the oscillator 74 of the delta data channel circuit 56a is free-running and provides a digital pulse train (i.e., time signal) at a relatively constant high frequency to the time counter 78. As such, the time signal is a digital representation of elapsed time. The time counter accumulates a "time count." The combination of the "data count" and the "time count" provides time-based digital information representative of the radiation passing through a subject during a scanning operation. In an alternate embodiment, the oscillator 74 and time counter 78 may be combined as a time circuit, separate from the delta data channel circuits 56a-56n, that is common to each delta data channel circuit.

In the embodiment being described, the data interval detector 80 receives the index signal from the encoder 44 and detects the rising edge generated during movement of the rotating gantry 14. Each pulse indicates the end of one data interval and the start of the next data interval. Each time the rising edge of a pulse is detected, the event is communicated to the delta data controller 82. The delta data controller 82 uses the combination of events detected by the data pulse detector 72 and data interval detector 80 to determine when to process the contents of the data counter 76 and the time counter 78 with the delta data processor 62 to develop the intensity value for each data interval. Since the time-based digital information developed by the signal processor 46 includes data from preceding and succeeding data intervals for a measured data interval, the delta data controller 82 and the delta data processor 62 may process information associated with three consecutive data intervals at any given time. The following description discusses how information for the three consecutive data intervals is processed by referencing the second, third, and fourth data intervals respectively. Information associated with the second data interval actually starts during a first data interval.

The delta data controller 82 communicates a "store" signal to the data counter 76 and time counter 78 each time a "pulse" is detected by the data pulse detector 72. The "store" signal directs the data counter 76 and time counter 78 to transfer their current values (i.e., "data count" and "time count") to the delta data storage circuit 60. The delta data controller 82 also communicates address information associated with the delta data storage circuit 60 identifying locations in the delta data storage circuit 60 where the data counter 76 and time counter 78 are to store their current values.

During the first data interval, the address information identifies storage locations for the "start data count" and the "start time" for the second data interval. In response to the store signal and address information, the data counter 76 stores its current value in the "start data count" location for the second data interval and the time counter 78 stores its current value in the "start time" location for the second data interval. If a subsequent "pulse" on the pulse data signal is detected before the next index pulse is detected by the data interval detector 80, the "start data count" and "start time" locations for the second data interval are overwritten in the same manner.

When the next index pulse is detected by the data interval detector 80, the rotating gantry 14 has reached the second data interval and the address information in the delta data controller 82 is altered to identify storage locations for the "start data count" and the "start time" for the third data interval. During the second data interval, each time the start of a "pulse" on the pulse data signal is detected by the data pulse detector 72, the delta data controller 82 communicates the "store" signal and associated address information to the data counter 76 and time counter 78 in the same manner as describe above. However, the data counter 76 stores its current value in the "start data count" location for the third data interval rather than overwriting the value stored for the second data interval. Likewise, the time counter 78 stores its current value in the "start time" location for the third data interval rather than overwriting the value stored for the first data interval. The "start data count" and "start time" locations for the third data interval are overwritten in the same manner if a subsequent "pulse" on the pulse data signal is detected before the next index pulse is detected by the data interval detector 80.

When the next index pulse is detected by the data interval detector 80, the rotating gantry 14 has reached the third data interval and the address information is altered to identify storage locations for the "end data count" and "end time" for the second data interval and the "start data count" and "start time" for the fourth data interval. When the start of a first "pulse" on the pulse data signal is detected during the third data interval, the delta data controller 82 communicates the "store" signal and associated address information to the data counter 76 and time counter 78 in the same manner as described above. However, the data counter 76 stores its current value in both the "end data count" location for the second data interval and the "start data count" location for the fourth data interval. Likewise, the time counter 78 stores its current value in both the "end time" location for the second data interval and the "start time" location for the fourth data interval. The "start data count," "end data count," "start time," and "end time" for the second data interval are now stored in the delta data storage circuit 60. At this point, the delta data controller 82 communicate a read signal and associated address information to the delta data processor 62. The read signal indicates that the stored "start data count," "start time," "end data count," and "end time" for the second data interval are ready to be read from the delta data storage circuit 60. The address information identifies the "start data count," "start time," "end data count," and "end time" locations from which to read the time-based digital information for the second data interval.

The delta data processor 62 subtracts the "start data count" from the "end data count" to determine the COUNT for the second data interval and subtracts the "start time" from the "end time" to determine the TIME for the second data interval. These values for COUNT and TIME relate to an average level of intensity for the combined offset current and analog data signals during the second data interval. The counts produced by the offset current are subtracted from the COUNT, and the result is divided by the TIME to determine the intensity of the detected radiation for the second data interval. The radiation intensity values for each detector and each data interval are stored in the radiation intensity storage circuit 64 awaiting reconstruction by the reconstruction processor 48. At this point, the delta data processor 62 may communicate a read signal and associated address information to the reconstruction processor 48. The read signal indicates that the stored radiation intensity value for the second data interval is ready to be read from the radiation intensity storage circuit 64. The address information identifies the location from which to read the radiation intensity value for the second data interval.

In another embodiment, the delta data processor 62 may accumulate the location information and communicate it along with the read signal either periodically or at the completion of a scanning operation. In still another embodiment, the radiation intensity values may be mapped into the radiation intensity storage circuit 64 in a manner such that the location information need not be communicated between the delta data processor 62 and the reconstruction processor 48. In this embodiment, the mapping of the radiation intensity storage circuit 64 is known to the reconstruction processor 48. Therefore, the reconstruction processor 48 only needs a read or ready signal from the delta data processor 62 or some other device indicating that either one or more radiation intensity values are stored or that the scanning operation is complete.

When the next index pulse is detected by the data interval detector 80, the rotating gantry 14 has reached the fourth data interval and the address information is altered to identify storage locations for the "end data count" and "end time" for the third data interval and the "start data count" and "start time" for a fifth data interval. When the start of a first "pulse" on the pulse data signal is detected during the fourth data interval, the data counter 76 stores its current value in both the "end data count" location for the third data interval and the "start data count" location for the fifth data interval in the same manner as described above for the second/fourth data intervals during the third data interval. Likewise, the time counter 78 stores its current value in both the "end time" location for the third data interval and the "start time" location for the fifth data interval. At this point, the "start data count," "end data count," "start time," and "end time" for the third data interval are now stored and the delta data controller 82 communicate a read signal and associated address information to the delta data processor 62 indicating such in the same manner as described above for the second data interval. The delta data processor 62 calculates a radiation intensity value for the third data interval and stores the radiation intensity value in the radiation intensity storage circuit 64 in the same manner as described above for the second data interval.

When the next index pulse is detected by the data interval detector 80, the rotating gantry 14 has reached the fifth data interval and the address information is altered to identify storage locations for the "end data count" and "end time" for the fourth data interval and the "start data count" and "start time" for a sixth data interval. When the start of a first "pulse" on the pulse data signal is detected during the fifth data interval, the data counter 76 stores its current value in both the "end data count" location for the fourth data interval and the "start data count" location for the sixth data interval in the same manner as described above for the second/fourth data intervals during the third data interval. Likewise, the time counter 78 stores its current value in both the "end time" location for the fourth data interval and the "start time" location for the sixth data interval. At this point, the "start data count," "end data count," "start time," and "end time" for the fourth data interval are now stored and the delta data controller 82 communicate a read signal and associated address information to the delta data processor 62 indicating such in the same manner as described above for the second data interval. The delta data processor 62 calculates a radiation intensity value for the fourth data interval and stores the radiation intensity value in the radiation intensity storage circuit 64 in the same manner as described above for the second data interval.

The process described above for the second, third, and fourth data intervals is repeated for each data interval during scanning operations as the rotating gantry 14 turns.

Figure 3:
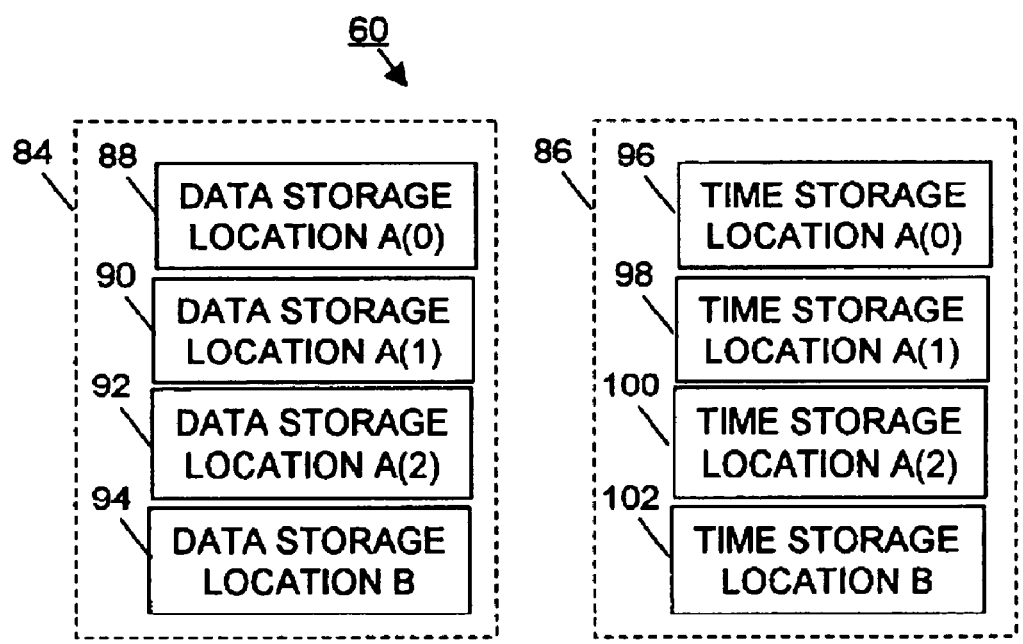
FIG. 3 is a block diagram of an embodiment of a storage circuit associated with the signal processor of FIG. 2.

With reference to FIG. 3, the delta data storage circuit 60 includes a data storage block 84 and a time storage block 86. For the embodiment of the signal processor 46 described above, the data storage block 84 and the time storage block 86 each include four data storage locations. More specifically, the data storage block 84 includes data storage location A(0) 88, data storage location A(1) 90, data storage location A(2) 92, and data storage location B 94. The time storage block 86 includes time storage location A(0) 96, time storage location A(1) 98, time storage location A(2) 100, and time storage location B 102.

With respect to the process described in reference to FIG. 2, the "start data count" for the second data interval is stored in data storage location A(0) 88 and the "start time" is stored in time storage location A(0) 96. The "end data count" for the second data interval is stored in data storage location B 94 and the "end time" in time storage location B 102. Similarly, the "start data count" for the third data interval is stored in data storage location A(1) 90 and the "start time" in time storage location A(1) 98. In the embodiment being described, the delta data processor 62 reads the "end data count" and "end time" for a measured data interval before the delta data controller 82 stores the "end data count" and "end time" for the next data interval. Therefore, the "end data count" for the third data interval is stored in data storage location B 94 and the "end time" in time storage location B 102. Likewise, the "start data count" for the fourth data interval is stored in data storage location A(2) 92, the "start time" in time storage location A(2) 100, the "end data count" in data storage location B 94, and the "end time" is in time storage location B 102.

There are many ways of implementing the delta data storage circuit 60 and the associated method for storing and reading the time-based digital information representing the intensity of the detected radiation during a scanning operation. In one embodiment, the delta data storage circuit 60 is comprised of four sets of data (C) and time (T) storage locations (e.g., storage registers). The storage locations depicted in FIG. 3 are identified in these four sets as follows: CA(0) 88 and TA(0) 96, CA(1) 90 and TA(1) 98, CA(2) 92 and TA(2) 100, and CB 94 and TB 102. The contents of the data counter 76 and time counter 78 are transferred to one or more of the four pairs of storage locations as follows. On detection of a "pulse" on the pulse data signal by the data pulse detector 56, the current values in the count and time counters are transferred to: a) CA(0) and TA(0) for data intervals DI(1), DI(4), DI(7), etc., b) CA(1) and TA(1) for data intervals DI(2), DI(5), DI(8), etc., and c) CA(2) and TA(2) for data intervals DI(3), DI(6), DI(9), etc. On detection of the first "pulse" of each data interval, the current values of count and time counters are also transferred to CB and TB. This provides the time-based digital information necessary to determine the intensity of the detected radiation during the preceding data interval and the stored "start data count," "end data count," "start time," and "end time" are read by the delta data processor 62.

In the embodiment being described, the DATA and TIME measurements for data intervals DI(2), DI(3), DI(4), and DI(5) are calculated by the delta data processor 62 as follows:

```
    DATA(2) = CB − CA(0)
    TIME(2) = TB − TA(0)
    (DATA and TIME measurements for DI(2) are calculated before
or at the end of DI(3).)
    DATA(3) = CB − CA(1)
    TIME(3) = TB − TA(1)
    (DATA and TIME measurements for DI(3) are calculated before
or at the end of DI(4).)
    DATA(4) = CB − CA(2)
    TIME(4) = TB − TA(2)
    (DATA and TIME measurements for DI(4) are calculated before
or at the end of DI(5).)
    DATA(5)=CB − CA(0)
    TIME(5) = TB − TA(0)
    (DATA and TIME measurements for DI(5) are calculated before
or at the end of DI(6).)
    The following pseudo code performs the DATA and TIME
measurements described above:
    Initialize flagB = 0
    for n=1:N
        while DI = n, upon receipt of a count pulse
            transfer counters to CA((n+2)(modulo3)) and
                TA((n+2)(modulo3))
            if flagB == 0
                transfer counters to CB and TB
                set flagB = 1
            end
        end
        DATA(n−1) = CB−CA((n)(modulo3)) and
        TIME(n−1) = TB−TA((n)(modulo3))
        reset flagB = 0
    end
```

Figure 4:
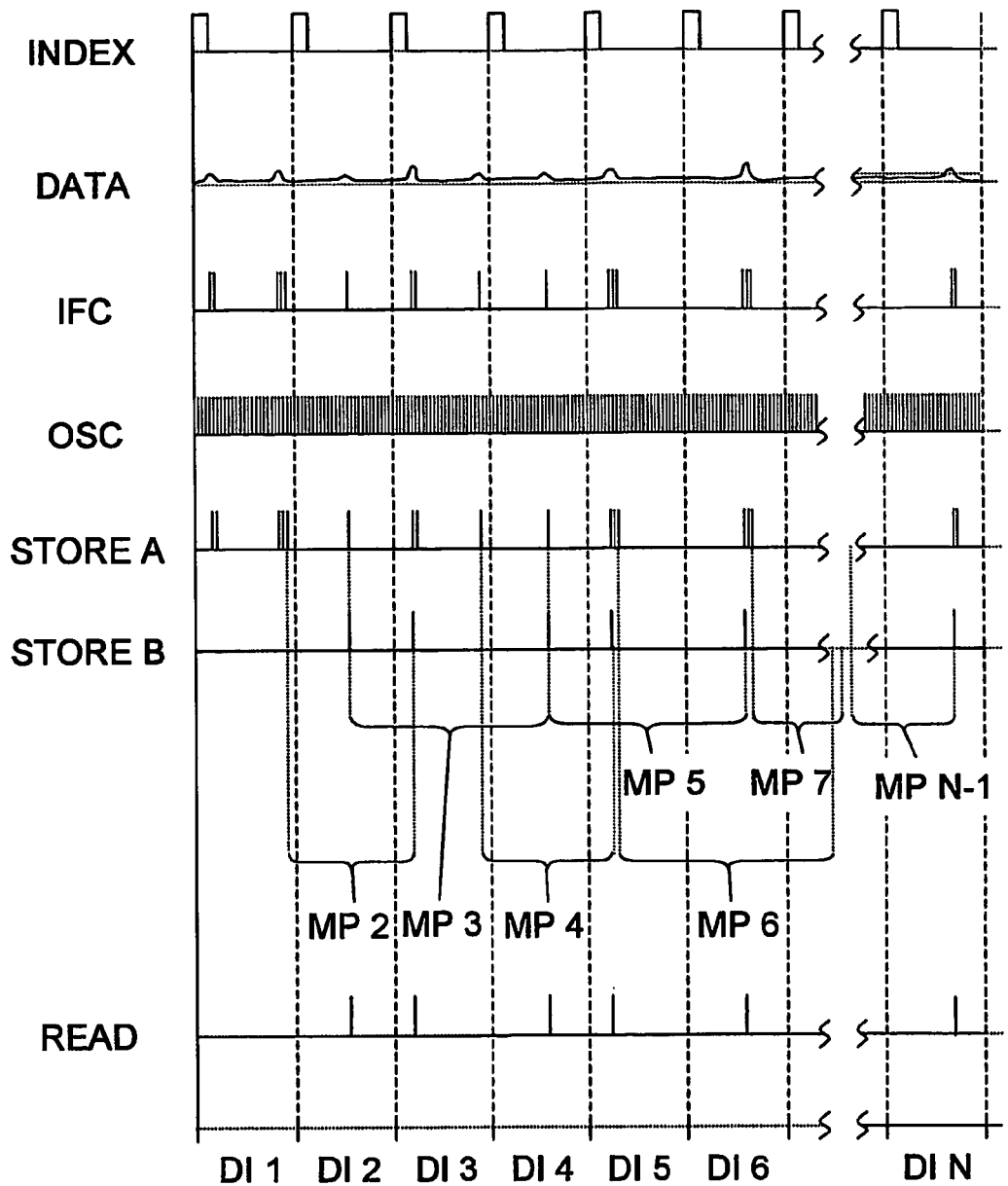
FIG. 4 is a timing diagram associated with an embodiment of the invention in which the measurement period for a data interval extends into adjacent preceding and succeeding data intervals.

With reference to FIG. 4, a sample timing diagram showing various signals within the embodiment of the CT scanner 10 described above during scanning operations. As shown, the timing diagram reflects signal levels during the first six data intervals (DI1-DI6) and the last data interval (DI N) of an exemplary detector. The INDEX signal represents the signal provided by the encoder 44 to the data interval detector 80 and defines the data intervals. As shown, the constant frequency of the pulses reflects the rotating gantry 14 moving at a constant velocity.

The DATA signal (i.e., offset data signal) represents the signal provided by the summing module 66 to the IFC 70 produced by combining the analog data signal from the radiation detector 40, 42 with the offset current from the offset module 68. The IFC signal (i.e., pulse data signal) represents the pulse train output of the IFC 70 that is provided to the data pulse detector 72 and data counter 76.

The OSC signal represents the free-running output of the oscillator 74 provided to the time counter 78. The resolution of the diagram does not permit identification of the frequency of the OSC signal. Nevertheless, the frequency of the pulses in the OSC signal is relatively constant at a predetermined very high frequency.

The STORE A signal represents the signal from the delta data controller 82 directing the data counter 76 and time counter 78 to store current values in start locations within the delta data storage circuit 60. Note that the STORE A signal is communicated each time a pulse is detected on the IFC signal during each data interval. The STORE A signal operates in conjunction with address information provided by the delta data controller 82 to the delta data storage circuit 60 to store the values of the counters in selected "start data count" and "start time" storage locations for measurement of the succeeding data interval.

The STORE B signal represents the signal from the delta data controller 82 directing the data counter 76 and time counter 78 to store current values in end locations within the delta data storage circuit 60. Note that the STORE B signal is communicated on the first pulse detected on the IFC signal during each data interval. The STORE B signal operates in conjunction with address information provided by the delta data controller 82 to the delta data storage circuit 60 to store the values of the counters in selected "end data count" and "end time" storage locations for measurement of the preceding data interval.

A pair of STORE A and STORE B signals identify the boundaries of the measurement period for a measured data interval. Note that the measurement period for a measured data interval starts in the preceding data interval when the last "pulse" on the DATA signal is detected and ends in the succeeding data interval when the first "pulse" on the DATA signal is detected. This can be seen by comparing the measurement periods to the time for the data interval, e.g., MP 2 to DI 2, MP 3 to DI 3, etc.

The READ signal represents the signal from the delta data controller 82 to the delta data processor 62 indicating that the "start data count," "end data count," "start time," and "end time" are stored for a measured data interval. The delta data processor 62 uses address information provided by the delta data controller 82 in conjunction with the READ signal to read the time-based digital information stored for the data interval.

In another embodiment of the method for storing and reading the time-based digital information, the offset current provided by the offset module 68 is reduced to a point where the delta data channel circuit 56a guarantees a "pulse" on the pulse data signal at least once during every 2½ data intervals. In this embodiment, the delta data storage circuit 60 is comprised of six pairs of data (C) and time (T) storage locations (e.g., storage registers). Four of these pairs are used to store "start data count" and "start time count" and two are used to store "end data count" and "end time count." The measurement periods can extend up to two data intervals preceding and two data intervals succeeding the measured data interval. That is, the start pulse may be two intervals before the measured data interval and the stop pulse may be two intervals after the measured data interval. The measurement period for a measured data interval starts with the last pulse preceding the measured data interval (i.e., within the two preceding data intervals) and terminates with the first pulse following the measured data interval (i.e., within the two succeeding data intervals). If no pulse is produced within the two preceding data intervals, the measurement period starts with the first pulse of the measured data interval or, if no pulse is produced within the two succeeding data intervals, the measurement period ends with the last pulse of the measured data interval. Data intervals can overlap by a greater amount at high attenuation, although on the average, the measurements will be centered on the current or measured data interval.

Figure 5:
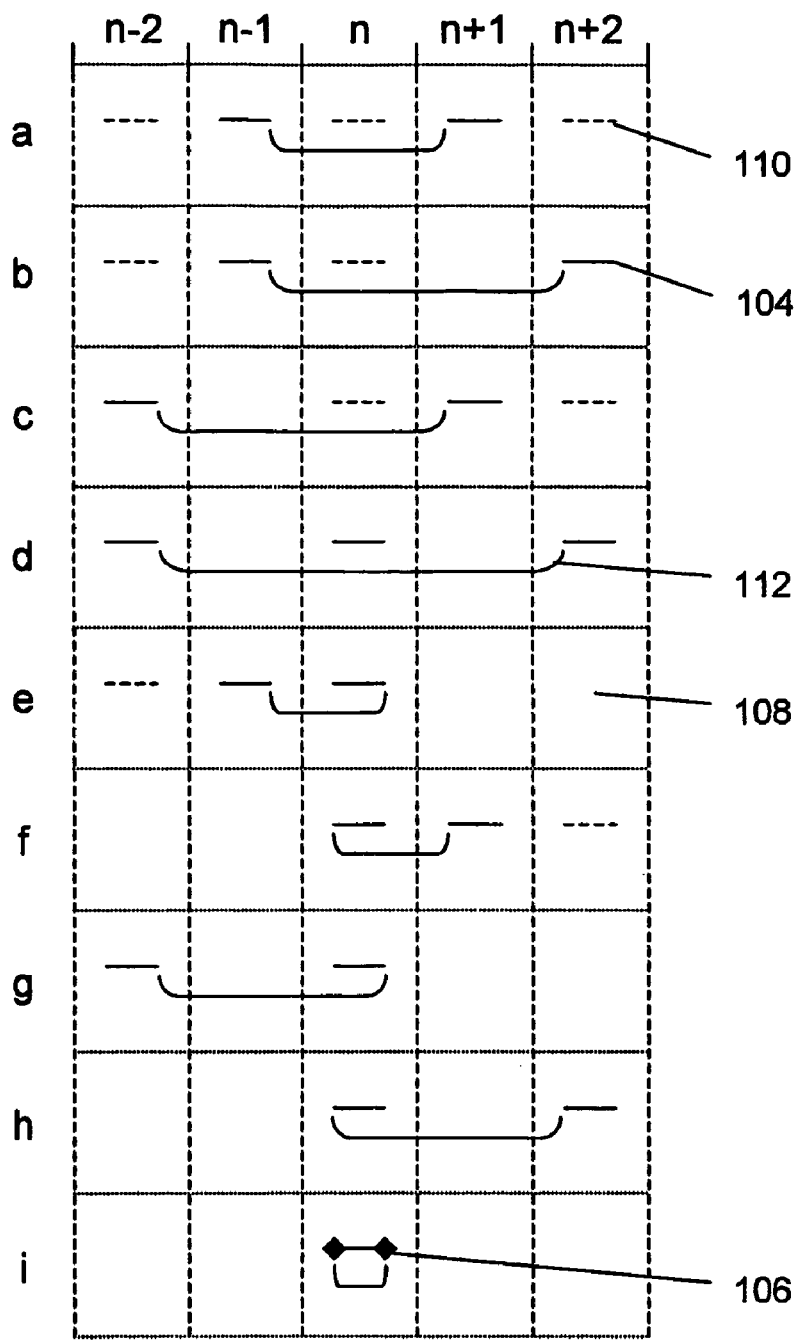
FIG. 5 is a timing diagram associated with another embodiment of the invention in which the measurement period for a data interval may extend into either of two preceding and either of two succeeding data intervals.

With reference to FIG. 5, a timing diagram shows various scenarios (i.e., scenarios a through i) for measurements periods associated with a measured data interval (n) for the embodiment having a "pulse" on the pulse data signal as least once during every 2½ data intervals. Two preceding data intervals are identified as n−2 and n−1. Two succeeding data intervals are identified as n+1 and n+2. If one or more data pulses are detected and the data interval includes a start or end boundary for a measurement period, a first line 104 is identified in the scenario. If two or more data pulses are detected and the data interval includes the start and end boundary for a measurement period, a second line 106 is identified in the scenario. If data pulses are not detected during a data interval, a blank data interval 108 is identified in the scenario. If it does not matter whether or not data pulses are detected during a data interval, a dashed line 110 is identified in the scenario. A measurement period with start and stop boundaries is identified by bracket 112 in each scenario.

If no data pulses are detected for three consecutive data intervals, an error condition exists for this embodiment. Scenario i creates a situation in which two or more data pulses are required during data interval n. Otherwise, only one pulse is required in a data interval used as a start or end boundary for the measurement period.

In an embodiment using storage locations, the storage location are identified in these six sets as follows CA(0) and TA(0), CA(1) and TA(1), CA(2) and TA(2), CA(3) and TA(3), CB(0) and TB(0), and CB(1) and TB(1). In general, the contents of the data counter 76 and time counter 78 are transferred to one or more of the four pairs of storage locations as follows.

On detection of a "pulse" on the pulse data signal by the data pulse detector 72, the contents of the data counter 76 and time counter 78 may, for example, be transferred to:

a) CA(0) and TA(0) for data intervals DI(3), DI(7), DI(11), etc., b) CA(1) and TA(1) for data intervals DI(4), DI(8), DI(12), etc., c) CA(2) and TA(2) for data intervals DI(5), DI(9), DI(13), etc., and d) CA(3) and TA(3) for data intervals DI(6), DI(10), DI(14), etc.

The pseudo code below for the embodiment with six pairs of data (C) and time (T) storage locations identifies additional storage combinations.

On detection of the first pulse within a data interval, the contents of the data counter 76 and time counter 78 may, for example, be transferred to:

a) CB(0) and TB(0) for data intervals DI(3), DI(5), DI(7), etc. and b) CB(1) and TB(1) for data intervals DI(4), DI(6), DI(8), etc.

The pseudo code below for the embodiment with six pairs of data (C) and time (T) storage locations identifies additional storage combinations.

This provides the time-based digital information necessary to determine the intensity of the detected radiation during a data interval for the embodiment being described. The stored "start data count," "end data count," "start time," and "end time" are read by the delta data processor 62 at the end of the second succeeding data interval.

The following pseudo code performs the DATA and TIME measurements for the embodiment described above with reference to FIG. 5:

```
initialize flagB(0) = 0; flagB(1) = 1
for n = 1:N
    while DI = n, upon receipt of a count pulse
        transfer counters to CA((n+1)(modulo4)) and
            TA((n+1)(modulo4))
        if flagB(0) == 0
        transfer counters to CB(0) and TB(0)
        end
        if flagB(1) == 0
        transfer counters to CB(1) and TB(1)
        end
        if flagB(0) AND flagB(1) == 0
            transfer counters to CA((n)(modulo4)) and
                TA((n)(modulo4))
        end
        set flagB(0)=1
        set flagB(1)=1
    end
    COUNT(n−2) = CB(n(modulo2)) − CA(n+2(modulo4))
    TIME(n−2) = TB(n(modulo2)) − TA(n+2(modulo4))
    transfer counters to CA((n+2)(modulo4)) and TA(n−2(modulo4))
        and to CB(n(modulo2)) and TB (n(modulo2))
    reset flagB(n(modulo2)) = 0
end
```

In summary, the various embodiments described above provide what may be referred to as a symmetrical delta data mode for measuring the intensity of detected radiation for data intervals during scanning operations in a CT scanner. The symmetrical delta data mode produces a measurement period for a measured data interval that extends into both the preceding and succeeding data intervals. On the average, the measurement period is centered on the measured data interval, thus producing an average skew of zero. As a result, artifacts due to data skewing are reduced from those of previous delta data modes. Moreover, under conditions of high attenuation, the measurement period is significantly longer than the data interval thus producing a more integrated signal and reducing quantum noise, thereby thus increasing the dynamic range of the overall.

The increase in measurement period as the input signal decreases produces an adaptive filtering effect in the analog domain that can potentially improve image quality more effectively than subsequent filtering in the digital domain. In various alternate embodiments, the offset current can be reduced to less than one "pulse" in the pulse data signal per data interval. The reduction in the offset current decreases shot noise associated with the offset current. In addition, reducing the offset current decreases the effects of quantization noise and 1/f noise. The resulting overall noise reduction improves image quality and can significantly extend the system dynamic range.

While the invention is described herein in conjunction with exemplary embodiments, it is evident that many alternatives, modifications, and variations will be apparent to those skilled in the art. Accordingly, the embodiments of the invention in the preceding description are intended to be illustrative, rather than limiting, of the spirit and scope of the invention. More specifically, it is intended that the invention embrace all alternatives, modifications, and variations of the exemplary embodiments described herein that fall within the spirit and scope of the appended claims or the equivalents thereof.

The invention claimed is:

1. A CT scanner, comprising:

a means for rotating a radiation source around an examination region;

a means for generating an analog data signal that varies with an intensity of radiation traversing the examination region;

a means for converting the analog data signal to a digital data signal including aperiodic pulses varying in frequency with the intensity of the radiation traversing the examination region as the radiation source rotates about the examination region and adding a minimized offset signal to the analog data signal prior to the converting so that the intensity of the analog data signal is such that at least one aperiodic pulse occurs on the digital data signal ever 2-½ data intervals;

a means for producing a time signal indicative of data intervals;

a means for determining average radiation intensity in each data interval by counting the pulses of the digital data signal starting with a digital data signal pulse occurring in a preceding data interval and continuing to a digital data signal pulse occurring in a succeeding data interval.

2. The CT scanner as set forth in claim 1, the time signal producing means further including:
  a means for detecting a start of a first measured data interval and a start of a next data interval.

3. The CT scanner as set forth in claim 2, the determining means further including:
  a means for storing a first digital data signal pulse count in a first start data location and storing a first time signal value associated with the first digital data signal pulse count in a first start time location each time a pulse occurs on the digital data signal until the first measured data interval starts and for storing a second digital data signal pulse count in an end data location and storing a second time signal value associated with the second digital data signal pulse count in an end time location when the next pulse occurs on the digital data signal after the start of the next data interval is detected;
  wherein the determining means determines the average intensity of the detected radiation for the first measured data interval by dividing a difference between the pulse count stored in the end data location and the pulse count stored in the first start data location by a difference between the value stored in the end time location and the value stored in the first start time location.

4. The CT scanner as set forth in claim 3 the converting means further including:
  a means for adding a minimized offset signal to the analog data signal so that the intensity of the analog data signal is such that at least one aperiodic pulse occurs on the digital data signal during each data interval;
  wherein the determining means considers the minimized offset signal when determining the average intensity.

5. The CT scanner as set forth in claim 1, the converting means further including:
  a means for adding a minimized offset signal to the analog data signal prior to the converting so that the intensity of the analog data signal is such that at least one aperiodic pulse occurs on the digital data signal every 2½ data intervals.

6. A method of measuring an intensity of detected radiation in a CT scanner, the method comprising:
  a) rotating a radiation source around an examination region;
  b) generating an analog data signal that varies with an intensity of radiation traversing the examination region;
  c) converting the analog data signal to a digital data signal including aperiodic pulses varying in frequency with the intensity of the radiation traversing the examination region as the radiation source rotates about the examination region and adding a minimized offset signal to the analog data signal prior to the converting so that the intensity of the analog data signal is such that at least one aperiodic pulse occurs on the digital data signal every 2½ data intervals;
  d) producing a time signal indicative of data intervals;
  e) determining average radiation intensity in each data interval by counting the pulses of the digital data signal starting with a digital data signal pulse occurring in a preceding data interval and continuing to a digital data signal pulse occurring in a succeeding data interval, and storing the average radiation intensity.

7. The method as set forth in claim 6 wherein step e) further includes:
  f) storing a first digital data signal pulse count in a first start data location and storing a first time signal value in a first start time location each time a pulse occurs on the digital data signal until a first measured data interval starts;
  g) detecting a start of the first measured data interval and detecting a start of a next data interval;
  h) after the start of the next data interval is detected, storing a second digital data signal pulse count in an end data location and storing a second time signal value in an end time location when the next pulse occurs on the digital data signal; and
  i) determining an average intensity of the detected radiation for the first measured data interval by dividing a difference between the pulse count stored in the end data location and the pulse count stored in the first start data location by a difference between the value stored in the end time location and the value stored in the first start time location.

8. The method as set forth in claim 7, further including:
  in step c), adding a minimized offset signal to the analog data signal prior to the converting so that the intensity of the analog data signal is such that at least one aperiodic pulse occurs on the digital data signal during each data interval; and
  in step i), considering the minimized offset signal when determining the average intensity.

9. The method as set forth in claim 7, further including:
  in step a), adding a minimized offset signal to the analog data signal prior to the converting so that the intensity of the analog data signal is such that at least one aperiodic pulse occurs on the digital data signal every 2½ data intervals;
  in step f), continuing to store the digital data signal pulse count in the same manner until the start of a second data interval;
  in step g), detecting a start of the second measured data interval between the start of the first measured data interval and the start of the next data interval; and
  in step i), determining the average intensity for the second measured data interval rather than the first measured data interval and considering the minimized offset signal when determining the average intensity.

10. The method as set forth in claim 1 wherein step e) further includes:
  f) storing a first digital data signal pulse count in a first star data location and storing a first time signal value in a first start time location each time a pulse occurs on the digital data signal during first and second preceding data intervals until a first measured data interval starts wherein the first preceding data interval is adjacent to the first measured data interval and the second preceding data interval is adjacent to the first preceding data interval.

11. The method as set forth in claim 10 wherein step e) further includes:

g) detecting a start of the first measured data interval and detecting a start of a first succeeding data interval adjacent to the first measured data interval;

h) after the start of the first succeeding data interval is detected, storing a second digital data signal pulse count in a first end data location and storing a second time signal value in a first end time location when the next pulse occurs on the digital data signal during the first succeeding data interval; and i) determining an average intensity of the detected radiation for the first measured data interval by dividing a difference between the pulse count stored in the first end data location and the pulse count stored in the first start data location by a difference between the value stored in the first end time location and the value stored in the first start time location.

12. The method as set forth in claim 10 wherein step e) further includes:

g) detecting a start of the first measured data interval, detecting a start of a first succeeding data interval adjacent to the first measured data interval, and detecting a start of a second succeeding data interval adjacent to the first succeeding data interval;

h) after the start of the second succeeding data interval is detected, storing a second digital data signal pulse count in a first end data location and storing a second time signal value in a first end time location when the next pulse occurs on the digital data signal during the second succeeding data interval; and i) determining an average intensity of the detected radiation for the first measured data interval by dividing a difference between the pulse count stored in the first end data location and the pulse count stored in the first start data location by a difference between the value stored in the first end time location and the value stored in the first start time location.

13. The method as set forth in claim 10 wherein step e) further includes:

g) detecting a start of the first measured data interval and detecting a start of a first succeeding data interval adjacent to the first measured data interval;

h) when the start of the first succeeding data interval is detected, storing a second digital data signal pulse count in a first end data location and storing a second time signal value in a first end time location; and i) determining an average intensity of the detected radiation for the first measured data interval by dividing a difference between the pulse count stored in the first end data location and the pulse count stored in the first start data location by a difference between the value stored in the first end time location and the value stored in the first start time location.

14. The method as set forth in claim 13 wherein:

the first succeeding data interval is a second measured data interval; and step e) further including:

j) storing a third digital data signal pulse count in a second start data location and storing a third time signal value in a second start time location each time a pulse occurs on the digital data signal during first and second preceding data intervals with respect to the second measured data interval until the second measured data interval starts, wherein the first preceding data interval is adjacent to the second measured data interval and the second preceding data interval is adjacent to the first preceding data interval;

wherein step e) further includes:

k) detecting a start of the second measured data interval and detecting a start of first and second succeeding data intervals with respect to the second measured data interval, wherein the first succeeding data interval is adjacent to the first measured data interval, wherein the second succeeding data interval is adjacent to the first succeeding data interval;

l) after the start of the second succeeding data interval is detected, storing a fourth digital data signal pulse count in a second end data location and storing a fourth time signal value in a second end time location when the next pulse occurs on the digital data signal during the second succeeding data interval; and m) determining an average intensity of the detected radiation for the second measured data interval by dividing a difference between the pulse count stored in the second end data location and the pulse count stored in the second start data location by a difference between the value stored in the second end time location and the value stored in the second start time location.

15. The method as set forth in claim 1 wherein step e) further includes:

f) detecting a start of the first measured data interval;

g) when the start of the first measured data interval is detected, storing a first digital data signal pulse count in a first start data location and storing a first time signal value in a first start time location.

16. The method as set forth in claim 15 wherein step e) further includes:

h) detecting a start of a first succeeding data interval adjacent to the first measured data interval;

i) after the start of the first succeeding data interval is detected, storing a second digital data signal pulse count in a first end data location and storing a second time signal value in a first end time location when the next pulse occurs on the digital data signal during the first succeeding data interval; and j) determining an average intensity of the detected radiation for the first measured data interval by dividing a difference between the pulse count stored in the first end data location and the pulse count stored in the first start data location by a difference between the value stored in the first end time location and the value stored in the first start time location.

17. The method as set forth in claim 16 wherein:

the first succeeding data interval is a second measured data interval; and step e) further including:

k) storing a third digital data signal pulse count in a second start data location and storing a third time signal value in a second start time location each time a pulse occurs on the digital data signal during first and second preceding data intervals with respect to the second measured data interval until the second measured data interval starts, wherein the first preceding data interval is adjacent to the second measured data interval and the second preceding data interval is adjacent to the first preceding data interval;

wherein step e) further includes:

l) detecting a start of the second measured data interval and detecting a start of a first succeeding data interval with respect to the second measured data interval, wherein the first succeeding data interval is adjacent to the second measured data interval;

m) when the start of the first succeeding data interval is detected, storing a fourth digital data signal pulse count in a second end data location and storing a fourth time signal value in a second end time location; and n) determining an average intensity of the detected radiation for the second measured data interval by dividing a difference between the pulse count stored in the second end data location and the pulse count stored in the second start data location by a difference between the value stored in the second end time location and the value stored in the second start time location.

18. The method as set forth in claim 15 wherein step e) further includes:

h) detecting a start of the first measured data interval, detecting a start of a first succeeding data interval adjacent to the first measured data interval, and detecting a start of a second succeeding data interval adjacent to the first succeeding data interval;

i) after the start of the second data interval is detected, storing a second digital data signal pulse count in a first end data location and storing a second time signal value in a first end time location when the next pulse occurs on the digital data signal during the second succeeding data interval; and j) determining an average intensity of the detected radiation for the first measured data interval by dividing a difference between the pulse count stored in the first end data location and the pulse count stored in the first start data location by a difference between the value stored in the first end time location and the value stored in the first start time location.

19. The method as set forth in claim 18 wherein:

the first succeeding data interval is a second measured data interval; and step e) further including:

k) storing a third digital data signal pulse count in a second start data location and storing a third time signal value in a second start time location each time a pulse occurs on the digital data signal during first and second preceding data intervals with respect to the second measured data interval until the second measured data interval starts, wherein the first preceding data interval is adjacent to the second measured data interval and the second preceding data interval is adjacent to the first preceding data interval;

wherein step e) further includes:

l) detecting a start of the second measured data interval and detecting a start of a first succeeding data interval with respect to the second measured data interval, wherein the first succeeding data interval is adjacent to the second measured data interval;

m) after the start of the first succeeding data interval is detected, storing a fourth digital data signal pulse count in a second end data location and storing a fourth time signal value in a second end time location when the next pulse occurs on the digital data signal during the first succeeding data interval; and n) determining an average intensity of the detected radiation for the second measured data interval by dividing a difference between the pulse count stored in the second end data location and the pulse count stored in the second start data location by a difference between the value stored in the second end time location and the value stored in the second start time location.

20. A method of measuring an intensity of detected radiation in a CT scanner, the method comprising:

rotating a radiation source around an examination region;

generating an analog data signal that varies with an intensity of radiation traversing the examination region;

converting the analog data signal to a digital data signal including aperiodic pulses varying in frequency with the intensity of the radiation traversing the examination region as the radiation source rotates about the examination region;

producing a time signal indicative of data intervals; and determining average radiation intensity in each data interval by counting the pulses of the digital data signal starting with a digital data signal pulse occurring in a preceding data interval and continuing to a digital data signal pulse occurring in a succeeding data interval, and storing the average radiation intensity, wherein determining includes:

storing a first digital data signal pulse count in a first start data location and storing a first time signal value in a first start time location each time a pulse occurs on the digital data signal until a first measured data interval starts;

detecting a start of the first measured data interval and detecting a start of a next data interval;

after the start of the next data interval is detected, storing a second digital data signal pulse count in an end data location and storing a second time signal value in an end time location when the next pulse occurs on the digital data signal; and determining an average intensity of the detected radiation for the first measured data interval by dividing a difference between the pulse count stored in the end data location and the pulse count stored in the first start data location by a difference between the value stored in the end time location and the value stored in the first start time location.

* * * * *